(12) United States Patent
Taran et al.

(10) Patent No.: US 8,501,152 B2
(45) Date of Patent: Aug. 6, 2013

(54) METHOD OF RADIOLABELLING CARBON NANOTUBES, RADIOLABELLED CARBON NANOTUBES AND APPLICATIONS THEREOF

(75) Inventors: Frëdëric Taran, Gif sur Yvette (FR); Dominique Georgin, Gif sur Yvette (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 410 days.

(21) Appl. No.: 12/741,709

(22) PCT Filed: Nov. 6, 2008

(86) PCT No.: PCT/FR2008/001560
§ 371 (c)(1),
(2), (4) Date: Aug. 16, 2010

(87) PCT Pub. No.: WO2009/092913
PCT Pub. Date: Jul. 30, 2009

(65) Prior Publication Data
US 2011/0038794 A1    Feb. 17, 2011

(30) Foreign Application Priority Data

Nov. 6, 2007   (FR) ..................................... 07 07782

(51) Int. Cl.
*A61K 51/00*   (2006.01)
*A61M 36/14*   (2006.01)

(52) U.S. Cl.
CPC ...................................... *A61K 51/00* (2013.01)
USPC ......................................... 424/1.11; 424/1.81

(58) Field of Classification Search
CPC ................................ A61K 51/00; A61M 36/14
USPC .......................................................... 424/1.11
See application file for complete search history.

(56) References Cited

U.S. PATENT DOCUMENTS 5,352,590 A * 10/1994 Kato et al. .................... 435/105
2005/0276742 A1   12/2005 Fan et al.
2007/0025918 A1    2/2007 Hurd

OTHER PUBLICATIONS

Yamago et al. (Chem. Biol. 1995, 2, 385-389).*
Tasis et al. (Chem. Rev. 2006, 106, 1105-1136).*
Peng et al. (J. Am. Chem. Soc. 2003, 125, 15174-15182).*

* cited by examiner

*Primary Examiner* — Michael G Hartley
*Assistant Examiner* — Melissa Perreira
(74) *Attorney, Agent, or Firm* — Morgan, Lewis & Bockius LLP (57) ABSTRACT

The present invention relates to a method of radiolabelling carbon nanotubes, to the radiolabelled carbon nanotubes that can be obtained by implementing this method, and to applications thereof.

21 Claims, 5 Drawing Sheets

METHOD OF RADIOLABELLING CARBON NANOTUBES, RADIOLABELLED CARBON NANOTUBES AND APPLICATIONS THEREOF

RELATED APPLICATIONS

The present application is a U.S. National Phase Application of International Application No. PCT/FR2008/001560 (filed Nov. 6, 2008), which claims priority of French Patent Application No. 0707782 (filed Nov. 6, 2007), all of which is hereby incorporated by reference in their entirety.

Carbon nanotubes (CNTs) were discovered in 1991 (Ijima S., Nature, 1991, 354, 54-56); since then, they have raised a great deal of interest, in particular owing to their mechanical properties: great mechanical strength (Treacy M. M. J. et al., Nature, 1996, 381, 678-680), electronic properties: conductor or semi-conductor property (Wildoer J. W. G. et al., Nature, 1998, 391, 59-62; Odom T. W. et al., Nature, 1998, 391, 62-64) and thermal properties.

Several methods of preparing CNTs have been described, including that of Ebbesen T. W. et al. (Nature, 1992, 358, 220-222), which makes it possible to obtain a high yield.

Figure 1:
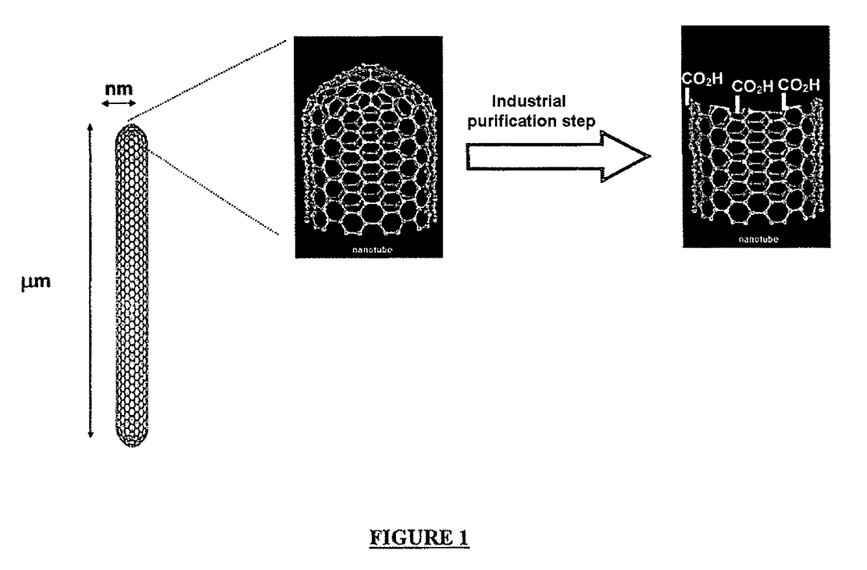
FIG. 1 is a diagrammatic representation of the step of industrial purification of carbon nanotubes generating surface carboxyl groups.

Methods of purifying CNTs have also been described (Hiura H. et al., Adv. Mater., 1995, 7, 275-276; Bonard J. M. et al., Mater., 1997, 9, 827-831 and Duesberg G. S. et al., Chem. Commun., 1998, 3, 435-436); these various methods make it possible to obtain desired amounts of CNTs. Specifically, the current methods of preparing CNTs generate a certain number of carbon-based impurities but also metal impurities that it is necessary to remove by means of purification steps. During these steps of purifying crude carbon nanotubes, carboxylic acids, which can be likened to aromatic carboxylic acids, are created at the surface of said CNTs, mainly at their ends (see attached FIG. 1 which is a diagrammatic representation of the carbon nanotube industrial purification step generating surface carboxylic groups). Most "native" CNTs are, however, sold and used in this form.

Depending on the technique and the conditions used, CNTs of various structures which vary according to the diameter, the length and also the linking of the carbon atoms can be prepared, in particular CNTs of small diameter, such as those sold under the trade name HiPco® by the company Carbon Nanotechnologies Inc. (CNI) or else those having "multi-wall" structures (Multi-Wall Carbon Nanotubes: MWCNTs) or "single-wall" structures (Single-Wall Carbon Nanotubes: SWCNTs) or graphite structures.

These various types of carbon nanotubes can, moreover, be in a completely, partially or not at all oxidized form.

From a chemical point of view, CNTs are therefore polymers composed only of carbon atoms and that can contain up to a million atoms. In accordance with the laws of carbon chemistry, the carbon atoms of a CNT are linked by means of a solid covalent bond and each atom has exactly three neighbors. Thus, whatever its length, a CNT is closed at its ends, so as to leave no free chemical bond at said ends. In general, the diameter of CNTs is usually between approximately 1 and 30 nm and their length can reach several micrometers.

From a physical point of view, CNTs can be defined as carbon crystals extending in a single direction, the repeating unit having the symmetry of a helix (Yakobson B. I. et al., American Scientist, 1997, 85, 324-337).

For several years, CNTs have found many applications, whether in the biology field (nanomedicine) or in the development of new materials, comprising field emission, energy storage, molecular electronics or atomic force microscopy. These applications most commonly belong to the field of fundamental research, but also industrial research. In this regard, some companies have already begun the large-scale production of CNTs.

Native CNTs are, however, difficult to solubilize in an aqueous solution. Thus, many biological applications require functionalization of the surface of native CNTs in order to provide them with aqueous solubility and certain biological or physical properties. Such applications include in particular the use of CNTs as DNA molecule biosensors, as protein transporters and biosensors, or else as ion channel blockers. Methods of chemical functionalization of CNTs are described in the prior art, in particular in the international application published under No. WO 97/32571.

All these observations therefore tend to promote the use of CNTs as an administration means for diagnostic or therapeutic molecules. In the face of this considerably rapid expansion, the question arises, however, of the impact of CNTs on the environment and health. Several in vitro studies suggest that the inhalation of CNTs can represent a significant risk to the lungs. Similarly, in vivo studies have demonstrated that, when they reach the lungs, CNTs (SWCNTs and MWCNTs) have the potential to cause substantial inflammatory reactions that can go as far as fibrosis. Thus, various authors have posed the question of the biocompatibility of CNTs in vivo, reviewing the various available results relating both to pulmonary toxicity and to skin irritation and to cytotoxicity that may be induced by CNTs (Smart S. K. et al., Carbon, 2006, 44, 1034-1047 and Monteiro-Riviere N. A. et al., Carbon, 2006, 44, 1070-1078). In addition, studies report that functionalization and the improvements which follow in terms of the aqueous solubility of CNTs, and consequently of the biocompatibility of these materials, considerably increase, however, the toxicity profiles observed in vitro (Sayes C. M. et al., Nano Lett., 2004, 4, 1881-1887 and Sayes C. M. et al., Toxicol. Lett., 2006, 161, 135-142).

However, no systematic study in vivo has been carried out in order to determine the toxicological and pharmacological profiles of CNTs, and the studies carried out to date give sketchy, sometimes contradictory, and also relatively inconclusive results, in particular owing to the use of various types of CNTs in various species of laboratory animals. Thus, with regard to what becomes of CNTs in vivo, the elimination or the binding thereof by the organs, the metabolization thereof or indeed the toxicity thereof, there are still as many questions as answers.

To address these questions, the use of fluorophores and especially the isotopic carbon labeling of CNTs remain tools of choice. A study of cell penetration in vitro has been carried out using CNTs labeled with fluorophores (Pantarotto D. et al., Chem. Commun., 2004, 16-17). More recently, a first study of the biodistribution of CNTs surface-labeled with diethylenetriaminepentacetic acid (DTPA)/$^{111}$In complexes has been carried out in mice by the same team (Singh R. et al., PNAS, 2006, 103(9), 3357-3362). This study has shown, in this particular case, that SWCNTs and MWCNTs thus labeled, which are soluble in water and biocompatible, have an improved toxicity profile compared with the same CNTs which are not functionalized.

Nevertheless, these labeling methods induce a modification of the structure of native CNTs which is not always acceptable. This is because the presence of radioactive complexes or of additional fluorophores grafted at the surface of CNTs can impair their intrinsic properties and, consequently, modify what becomes of CNTs both in vitro and in vivo. In addition, the presence of these relatively hindering complexes at the surface of CNTs may limit or even prevent subsequent functionalization thereof with reagents of interest.

Thus, the inventors have given themselves the objective of providing a novel method of labeling carbon nanotubes which does not induce a modification of the structure of the CNTs, in order to allow the identification of the toxicological and pharmacological profiles of CNTs in vitro and in vivo, without limiting the possibilities of subsequent functionalization of these CNTs according to the applications envisioned.

The method in accordance with the present invention is based on covalent, and therefore stable, radiolabeling of CNTs, consisting in substituting the carbon 12 ($^{12}$C) atoms of one or more carboxyl groups present at the surface of native CNTs with carbon 13 ($^{13}$C) or carbon 14 ($^{14}$C) atoms, without inducing a structural modification of their surface.

A first subject of the present invention is therefore a method of radiolabeling carbon nanotubes comprising one or more surface carboxyl groups, characterized in that it comprises at least the following steps:

a) a step of substituting the surface carboxyl groups with radiolabeled nitrile groups, consisting in reacting, in an organic solvent, said carbon nanotubes with a carbon 13-radiolabeled or carbon 14-radiolabeled cyanide, in the presence of a palladium catalyst, so as to result in radiolabeled carbon nanotubes comprising, at the surface, one or more carbon 13-labeled or carbon 14-labeled nitrile groups; and b) a step of hydrolyzing the nitrile group(s) consisting in reacting, in an organic solvent or in a mixture of water and of at least one organic solvent, the carbon nanotubes obtained above in step a) with an acid or a base so as to result in radiolabeled carbon nanotubes comprising, at the surface, one or more carboxyl groups in which the carbon atom bearing the acid function is a carbon 13 or carbon 14 atom.

Such a method can be represented by the following reaction scheme A:

SCHEME A

-continued in which:
    the honeycomb mesh represents a part of the carbon polymer forming the structure of the carbon nanotube;
    *C represents a carbon 13 or carbon 14 atom;
it being understood that, on this scheme, a single surface group has been represented for reasons of convenience of the drawing and of illustration, but that the method in accordance with the invention obviously applies to carbon nanotubes comprising one or more surface carboxyl groups.

The method of radiolabeling in accordance with the present invention has the advantage of not inducing a structural modification of CNTs. The radioactivity is, in addition, directly associated with the CNT itself and not with reagents or complexes grafted onto its surface. Thus, the intrinsic properties of the CNTs remain unchanged and remain particularly stable over time. Furthermore, the unmodified surface of the radiolabeled CNTs obtained in accordance with the method of the invention then allows full scope of subsequent grafting of functional groups for conferring particular biological and/or enzymatic properties on the radiolabeled CNTs.

According to a first particular embodiment of the method in accordance with the present invention, substitution step a) is carried out in a single step, by cyanating decarboxylation of the surface carboxyl groups in the presence of a palladium catalyst, preferably chosen from palladium (II) ($Pd^{II}$) salts.

According to said embodiment, the $Pd^{II}$ salts are, for example, chosen from palladium trifluoroacetate (Pd(OCOCF$_3$)$_2$), palladium sulfate (PdSO$_4$) and palladium nitrate (Pd(NO$_3$)$_2$).

According to a preferred embodiment of said first embodiment, the solvent a) is chosen from dimethylformamide (DMF), dimethyl sulfoxide (DMSO) and water, and mixtures thereof.

According to a particularly preferred embodiment of said first embodiment, the organic solvent a) is DMF alone or a DMF/DMSO mixture, in a volume ratio ranging from 100/0 to 80/20 approximately, and even more preferably in a volume ratio of 95/5 approximately.

According to another preferred embodiment of this first embodiment, cyanating decarboxylation step a) is carried out at a temperature of 25 to 150° C. approximately, and even more preferably at a temperature of approximately 120° C.

According to yet another preferred embodiment of this first embodiment, cyanating decarboxylation step a) is carried out in the presence of a silver or copper salt that may in particular be chosen from silver carbonates, nitrates and triflates or copper carbonates, nitrates and triflates.

According to the invention, the duration of cyanating decarboxylation step a) can range from 1 to 12 hours approximately. The duration of step a) is even more preferably 3 hours approximately.

According to a second particular embodiment of the method in accordance with the present invention, substitution step a) comprises the following three substeps:
a1) a substep of substituting the hydroxyl groups of said surface carboxyl groups with halide groups, consisting in reacting said carbon nanotubes with a halogenating agent, optionally in the presence of a solvent, so as to result in carbon nanotubes comprising, at the surface, one or more acid halide groups;
a2) a second substep of substituting the halogen atom of said acid halide groups with a radiolabeled nitrile group, consisting in reacting, in an organic solvent, the carbon nanotubes obtained above in step a1) with a carbon 13-radiolabeled or carbon 14-radiolabeled cyanide, so as to result in radiolabeled carbon nanotubes comprising, at the surface, one or more carbon 13-labeled or carbon 14-labeled ketonitrile groups;
a3) a third substep of decarbonylating said ketonitrile groups, consisting in reacting, in an organic solvent, the radiolabeled carbon nanotubes obtained above in step a2) in the presence of a catalyst chosen from) palladium$^0$ ($Pd^0$) salts and complexes, so as to result in radiolabeled carbon nanotubes comprising, at the surface, one or more carbon 13-labeled or carbon 14-labeled nitrile groups.

According to this second embodiment, the halogenating agent used in substep a1) is preferably chosen from thionyl dichloride (SOCl$_2$), oxalyl chloride (ClCOCOCl), phosphorus trichloride (PCl$_3$) and phosphorus pentachloride (PCl$_5$). According to a particular embodiment of this method of preparation, it should be noted that, when the halogenating agent used in substep a1) is thionyl dichloride, it also serves as an organic solvent, making it needless to use an additional organic solvent.

Still according to this second embodiment, the palladium$^0$ salts and complexes used in substep a3) are preferably chosen from the salts of $Pd^{II}$ in the presence of a ligand of phosphine type. These salts generate palladium$^0$ in situ. Among such salts, mention may more particularly be made of tetrakis (triphenylphosphine)palladium (Pd(Phh$_3$)$_4$), and also those among the pairings palladium$^{II}$ acetate/triphenylphosphine (Pd(OAc)$_2$/TPP), palladium$^{II}$ acetate/tributylphosphine (Pd(OAc)$_2$/TBP) and palladium$^{II}$ acetate/tricyclohexylphosphine (Pd(OAc)$_2$/PCy$_3$).

The organic solvent(s) that can be used for carrying out substeps a1), a2) and a3) are preferably chosen from toluene, acetonitrile, benzene, dimethylformamide (DMF) and dioxane, and mixtures thereof.

According to a particularly preferred embodiment of this second embodiment, step a3) is carried out in the presence of a nucleophilic compound which makes it possible to very significantly improve the yield of conversion of the ketonitrile group to a nitrile group.

According to the invention, the term "nucleophilic compound" is intended to mean any chemical compound attracted by positively charged species and which has a nonbonding doublet.

In this case, the nucleophilic compound is preferably chosen from cesium fluoride (CsF), potassium fluoride (KF) and potassium cyanide (KCN).

According to another preferred embodiment of this second embodiment, step a1) is carried out at a temperature of 25 to 120° C., and even more preferably at a temperature of 70° C. approximately; step a2) is carried out at a temperature of 25 to 120° C., and even more preferably at a temperature of 25° C. approximately, and step a3) is carried out at a temperature of 50 to 120° C., and even more preferably at a temperature of 110° C. approximately.

According to an advantageous embodiment of implementation of the method in accordance with the invention, substep a2) is carried out in the presence of an iodide salt such as, for example, sodium iodide, tetrabutylammonium iodide (I$^-$N$^+$Bu$_4$) and potassium iodide.

For the purpose of the present invention, the term "cyanide" is intended to mean cyanide as such and also derivatives thereof.

According to the invention, the radiolabeled cyanide is preferably chosen from cyanide, trimethylsilyl cyanide, metal cyanides such as, for example, potassium cyanide (KCN), cuprous cyanide (CuCN), silver cyanide (AgCN) and zinc cyanide (Zn(CN)$_2$), it being understood that, in these cyanides, the carbon atom involved in the triple bond with the nitrogen atom is a carbon 13 or carbon 14 atom, and from the cyanide derivatives of formula (I) below:

(I)

in which:
R$_1$ and R$_2$, which may be identical or different, represent a C$_1$-C$_4$ alkyl radical, or else R$_1$ and R$_2$ form, together with the carbon atom to which they are attached, a hexane ring; and
*C represents a carbon 13 or carbon 14 atom.

As compound of formula (I) above, mention may in particular be made of carbon 13-labeled or carbon 14-labeled acetone cyanohydrin and carbon 13-labeled or carbon 14-labeled cyclohexanone cyanohydrin.

Step b) of hydrolyzing the surface nitrile groups can be carried out under acidic conditions (acid hydrolysis) or under alkaline conditions (alkaline hydrolysis).

When it is an acid hydrolysis, step b) is carried out in the presence of an acid that can in particular be chosen from sulfuric acid, hydrochloric acid, formic acid, hydrobromic acid, and acetic acid in the presence of boron trifluoride.

When it is an alkaline hydrolysis, step b) is carried out in the presence of a base that can in particular be chosen from strong bases such as potassium hydroxide (KOH), sodium hydroxide (NaOH) and tetrabutylammonium hydroxide. These bases are preferably used in aqueous solutions or in aqueous-alcoholic solutions, for example in solutions in a mixture of water and ethanol.

According to a preferred embodiment of the labeling method in accordance with the present invention, the carbon nanotubes undergo one or more washing and/or sonication steps, the latter occurring between the various steps and substeps of the method and/or at the end of step b) of hydrolyzing the nitrile groups.

The washing operations are preferably carried out with a solvent chosen from water, acidic aqueous solutions such as, for example, a solution of hydrochloric acid (in particular 5%), basic aqueous solutions such as, for example, aqueous solutions of ammonia, and organic solvents such as DMSO, ether, toluene and lower alcohols such as ethanol.

According to a particularly advantageous embodiment of the method in accordance with the invention, each washing step consists of addition of the solvent, followed by dispersion of the nanotubes by sonication, and then of a centrifugation followed by pipetting of the supernatant in order to remove the possible impurities.

Once they have been prepared, the radiolabeled nanotubes thus obtained are preferably dried, for example using a rotary evaporator.

A subject of the present invention is also the radiolabeled carbon nanotubes that can be obtained by implementing the method in accordance with the present invention, characterized in that they comprise one or more surface carboxyl groups in which the carbon atom bearing the acid function is a carbon 13 or carbon 14 atom.

According to the present invention, these radiolabeled nanotubes generally have a diameter ranging from 0.8 to 15 nm approximately. The length of these nanotubes can, moreover, range from 0.1 to 10 μm approximately.

The structure of the nanotubes in accordance with the present invention may, for example, be a single-wall structure (SWCNTs) or a multi-wall structure (MWCNTs).

The radiolabeled CNTs in accordance with the present invention have the advantage of being radiolabeled in their native state, and can therefore be subsequently functionalized as required or according to the desired application.

Thus, according to one variant of the invention, the radiolabeled nanotubes comprise, at their surface, one or more functional reactants bonded, by means of a covalent bond, to at least one of the oxygen atoms of the radiolabeled carboxyl groups.

As functional reactants that can be grafted onto the radiolabeled nanotubes in accordance with the invention, mention may in particular be made of diazoniums, nitrenes, carbenes and pyrrolidines.

Thus, a radiolabeled CNT according to the invention may be used for varied applications, in particular in the case where the nanotubes are functionalized, depending on the type of reactant grafted at its surface.

Figure 2:
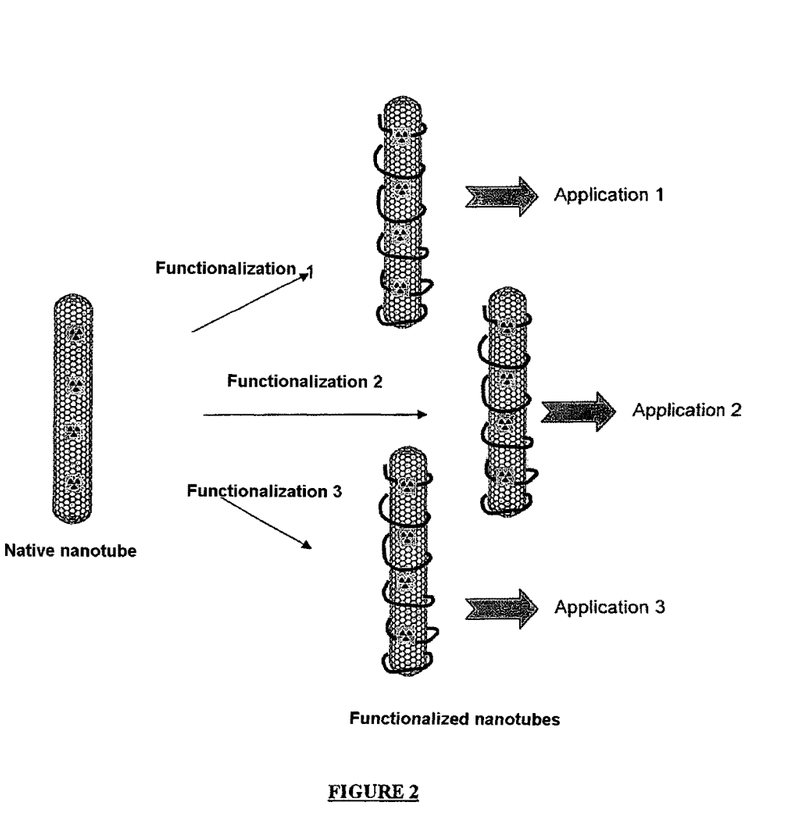
FIG. 2 is a diagrammatic representation of the advantage of the radiolabeling of functionalized carbon nanotubes.

A subject of the invention is therefore also the use of the radiolabeled carbon nanotubes as defined above, as diagnostic tools, in particular for:

studying the metabolism and/or the biodistribution of carbon nanotubes in vivo (determination of the pharmaceutical profiles);

studying the cell penetration of nanotubes in vivo;

studying what becomes of carbon nanotubes in the environment;

for investigating molecules of interest (targeted diagnosis); as illustrated in the attached FIG. 2 which is a diagrammatic representation of the advantage of the radiolabeling of functionalized carbon nanotubes.

In addition to the above arrangements, the invention also comprises other arrangements which will emerge from the additional description which follows, which relates to examples of preparing radiolabeled nanotubes in accordance with the method which is the subject of the invention, to examples demonstrating the effectiveness of the radiolabeling on various carbon nanotube structures, and also to the attached drawings in which.

EXAMPLE 1

Preparation of Carbon 14-Radiolabeled Carbon Nanotubes 20 mg of native single-wall carbon nanotubes (SWCNTs) comprising surface carboxyl groups, sold under the trade name P3-SWNT by the company Carbon Solution Inc., 1.08 mg of carbon 14-labeled potassium cyanide (K$^{14}$CN), 14 mg of silver carbonate Ag$_2$CO$_3$ and 1.1 mg of Pd(COCF$_3$)$_2$ were added to 10 ml of a DMF/DMSO mixture (95/5: v/v). The reaction mixture was stirred at a temperature of 120° C. for 3 hours in a round-bottom flask fitted with a condenser.

After cooling, the reaction medium was concentrated by means of a rotary evaporator. The nanotubes were then washed with water (10×10 ml), with hydrochloric acid diluted to 5% in water (8×10 ml), with DMSO (9×10 ml) and then with ether (5×10 ml). Between each washing step, the nanotubes were redispersed by sonication and then centrifuged, and the centrifugation supernatant was drawn off by pipetting so as to remove the possible impurities.

The carbon nanotubes thus obtained were then heated for 18 hours with stirring in a mixture of 4 ml of potassium hydroxide at 40% in water and 4 ml of absolute ethanol. The mixture was then acidified to pH 5 with 4 N hydrochloric acid.

At the end of the hydrolysis, the carbon nanotubes were washed with water (1×10 ml) and then dried in a rotary evaporator. 9.2 mg of radiolabeled nanotubes (CNT-1) were obtained, for which the specific radioactivity incorporated was measured using a counter sold under the trade name Wallac® 1409 by the company Perkin Elmer Life Science.

The same method was also used to radiolabel 10 mg of carbon nanotubes of small diameter (0.8 to 1.3 nm) sold under the trade name HiPco® by the company Carbon Nanotechnologies Inc. 6 mg of radiolabeled nanotubes (CNT-2) were obtained, for which the specific radioactivity incorporated was also measured using the Wallac® 1409 counter.

The specific radioactivity of the CNT-1 and CNT-2 nanotubes is reported in table 1 hereinafter:

TABLE 1

| Nanotubes | Specific radioactivity (μCi/mg) |
|---|---|
| CNT-1 | 0.35 |
| CNT-2 | 0.4 |

EXAMPLE 2

Preparation of Carbon 14-Radiolabeled Carbon Nanotubes 50 mg of native single-wall carbon nanotubes (SWCNTs) comprising surface carboxyl groups, sold under the trade name P3-SWNT by the company Carbon Solution Inc. were added to 10 ml of thionyl chloride, and then the mixture was stirred at a temperature of 70° C. for 18 hours.

The reaction medium was then completely evaporated off by means of a rotary evaporator, and then 20 ml of acetonitrile, 45 mg of carbon 14-labeled cuprous cyanide (Cu$^{14}$CN) and 150 mg of sodium iodide (NaI) were added. The mixture was stirred at ambient temperature for 18 hours. The sodium iodide was then extracted by washing with acetone (2×10 ml), and then the reaction medium was again completely evaporated off.

The carbon nanotubes thus obtained were then taken up in 20 ml of toluene, to which 213 mg of Pd(PPh$_3$)$_4$ and 30 mg of cesium fluoride (CsF) were added. The reaction mixture was stirred at a temperature of 110° C. for 5 hours.

A washing-sonication-pipetting series was carried out as previously described above in example 1, using toluene (2×10 ml), an aqueous solution of ammonia at 10% (2×10 ml), water (2×10 ml) and ethanol (2×10 ml).

The radiolabeled carbon nanotubes thus obtained were then heated for 18 hours with stirring in a mixture of 4 ml of potassium hydroxide at 40% in water and 4 ml of absolute ethanol. The mixture was then acidified to pH 5 with 4 N hydrochloric acid.

At the end of the hydrolysis, the carbon nanotubes were washed with water (2×10 ml) and then dried in a rotary evaporator. 19.0 mg of radiolabeled nanotubes (CNT-3) were obtained, for which the specific radioactivity incorporated was measured using the counter from the company Ludlum, model 2200.

By way of comparison, 50 mg of the same P3-SWNT carbon nanotubes were also radiolabeled according to the method which has just been described above in this example, but without using cesium fluoride (CNT-4). The specific radioactivity of the CNT-4 was also measured using the Ludlum counter, model 2200.

The same method was also used to radiolabel 50 mg of native multi-wall carbon nanotubes (MWCNTs) comprising surface carboxyl groups, sold under the trade name MWCNT-Graphistrength® by the company Arkema (in the presence of cesium fluoride). 13 mg of radiolabeled nanotubes (CNT-5) were obtained, for which the specific radioactivity incorporated was also measured using the Ludlum counter, model 2200.

The specific radioactivity of the CNT-3, CNT-4 and CNT-5 nanotubes is reported in table 2 hereinafter:

TABLE 2

| Nanotubes | Specific radioactivity (μCi/mg) |
|---|---|
| CNT-3 (with CsF) | 7.3 |
| CNT-4 (without CsF) | 5 |
| CNT-5 (with CsF) | 58 |

All these results show, firstly, that the radiolabeling method in accordance with the present invention actually makes it possible to prepare radiolabeled carbon nanotubes with good radioactivity incorporation results, whatever the type of carbon nanotube used.

These results also show that, when the method is carried out according to the second variant thereof (implementation of substeps a1) to a3)), the labeling efficiency is improved (comparisons of the radioactivities measured for CNT-1 and CNT-2 compared with CNT-3 to CNT-5) and that the presence of a nucleophilic compound during the implementation of substep a3) makes it possible to further improve the radiolabeling efficiency (comparison of the specific radioactivities measured on CNT-3 and CNT-4).

It should be clearly understood, however, that, in the examples above, the use of carbon 14-labeled reactive cyanides is not limiting. Radiolabelings with carbon 13 were carried out under the same conditions, and made it possible to also obtain very good results in terms of specific activity.

TABLE 3

Examples of carbon nanotubes radiolabeled by means of the methods of the invention.

| | CNT | | | | | Specific |
|---|---|---|---|---|---|---|
| Origin | Nature | L (μm) | D (nm) | CO$_2$H (%) | Method | activity |
| CNI | Hipco ® | 1-10 | 0.8-1.3 | ? | E1 | 0.4 μCi/mg |
| CNI | Hipco ® | 1-10 | 0.8-1.3 | ? | E2 | 25 μCi/mg |
| Carbon solution Inc. | SWCNT | 0.5-1.5 | 1.4 | ~5 | E1 | 0.35 μCi/mg |
| Carbon solution Inc. | SWCNT | 0.5-1.5 | 1.4 | ~5 | E2 | 7.3 μCi/mg |
| Arkema | MWCNT | 0.1-10 | 10-15 | ? | E2 | 58 μCi/mg |
| Nanothinx | MWCNT | ~10 | 18-35 | 10 | E2 | 13 μCi/mg |
| CEA | MWCNT | 0.2-4 | 20 | ~5 | E2 | 12 μCi/mg |

SWCNT = single-wall nanotubes;
MWCNT = multi-wall nanotubes;
L = length;
D = diameter;
E1 = procedure of example 1;
E2 = procedure of example 2.

EXAMPLE 3

Efficiency and Generality of the Method

The labeling methods of the invention were applied to several types of carbon nanotubes. The results obtained, which are given in table 3 below, confirm that the most efficient method is the "decarbonylation" method. Said method is applicable to nanotubes of any type, whether they are single-wall or multi-wall, and of variable size (diameter, length).

The advantages of this method are therefore: i) the generality of the method, ii) the absence of structural modification related to the labeling, iii) the preservation of the carboxylic acids which are often used to functionalize the nanotubes (by means of peptide bonds, for example).

EXAMPLE 4

Figure 3:
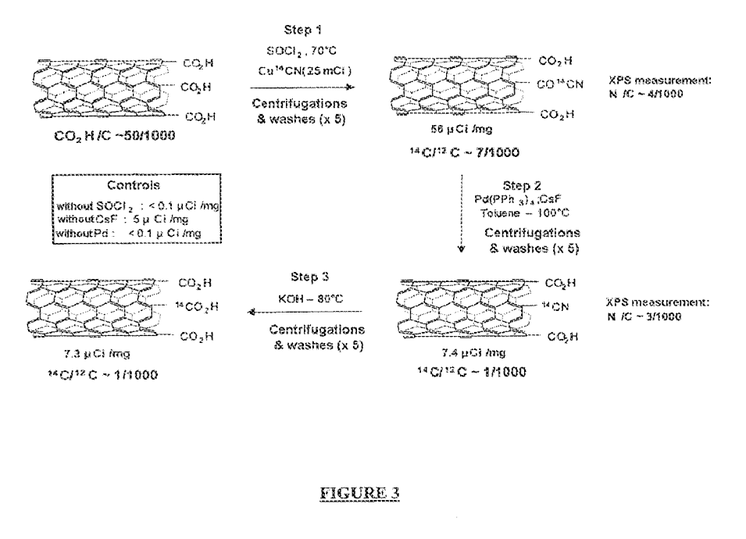
FIG. 3 is a diagrammatic representation of the labeling method of example 2 and of the control steps performed in example 4.

Studies were undertaken in order to provide analytical elements making it possible to validate the method of example 2. These studies were essentially carried out on the single-wall nanotubes (reference P3-SWCNT from the company Carbon Solution Inc.). The method of example 2 was used, said method using the carboxylic acids present at the surface and especially at the ends of the nanotubes. The radioactivity associated with the nanotubes was measured after each step required for the labeling. This measurement gives orders of magnitude of the radiolabeling efficiency (FIG. 3). Thus, it is noted, for nanotubes comprising approximately 5% of carboxylic acid functions, that approximately one atom is introduced per 1000 $^{12}$C atoms which corresponds to a labeling of approximately 2% of the carboxylic acids present. Control experiments carried out without certain chemical ingredients necessary for the labeling ($SOCl_2$ and $Pd^0$) clearly show the absence of labeling. This observation confirms the existence of covalent labeling. Finally, a control experiment carried out without fluoride ion (CsF) shows a lower labeling efficiency, which confirms the beneficial (but not essential) role of this chemical additive.

A $^{13}C$-labeling was also carried out on the same batch of nanotubes in order to be able to perform additional analyses. The surface elemental analysis (XPS, FIG. 3) gives a nitrogen/carbon ratio of the same order of magnitude as the $^{14}C/^{12}C$ ratio. Nitrogen is an atom that is normally absent from nanotubes; said nitrogen could therefore have been introduced only by the labeling method of the invention, and with the same degree of efficiency as the $^{14}C$.

Figure 4:
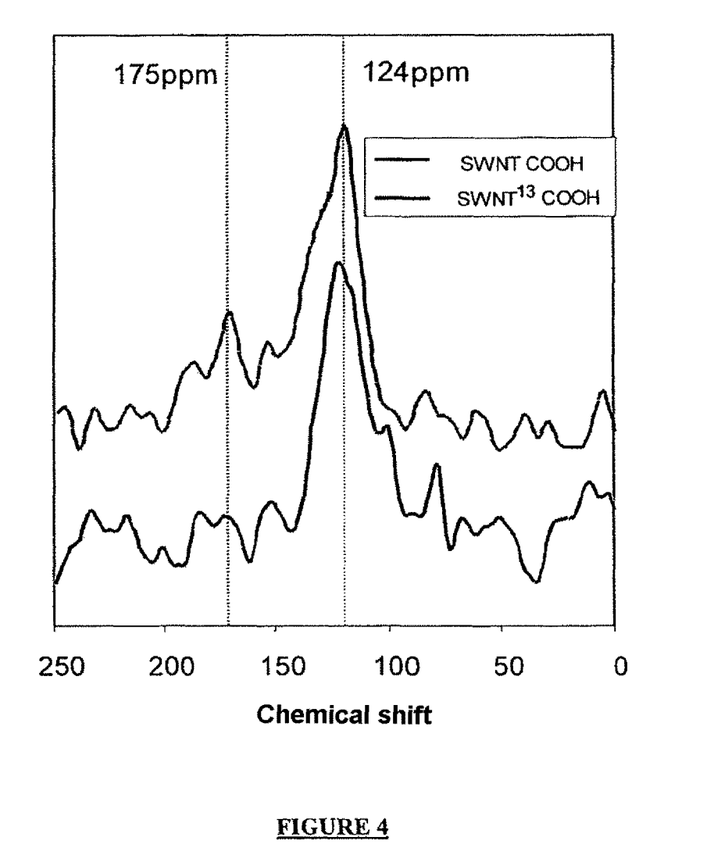
FIG. 4 represents the solid-state ($^{13}$C) NMR spectrum of single-walled nanotubes obtained before and after $^{13}$C-labeling of the nanotubes by means of the method of example 2.

Finally, solid-state NMR studies were carried out on the same batch of nanotubes before and after $^{13}C$-labeling. According to the $^{14}C$-labeling results previously obtained, approximately 2% of the carboxylic acids are labeled at the end of the method. An increase in the NMR signal corresponding to the chemical shift of the carboxylic acids ($\lambda$=175 ppm) following the $^{13}C$-labeling is actually observed (FIG. 4).

EXAMPLE 5

Use of the $^{14}C$-Radiolabeled Nanotubes for In Vivo Studies

Studies of biodistribution of radiolabeled nanotubes, in rodents, were carried out in order to be sure that the labeling efficiency made it possible to monitor these nanoparticles in vivo for applications in toxicology. Two methods of contamination (nasal instillation and intravenous injection) and two methods of imaging (whole body and collection of organs) were used.

Figure 5:
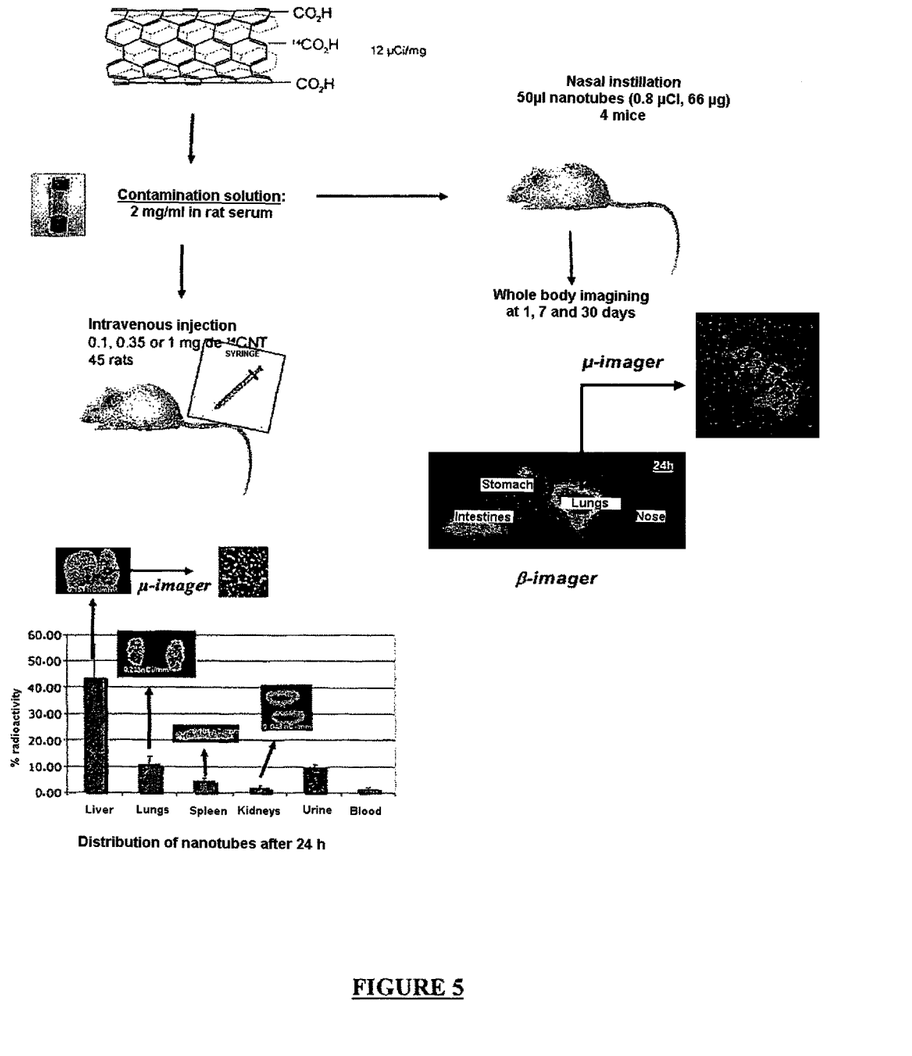
FIG. 5 is a diagrammatic representation of the uses which can be made of the radiolabeled carbon nanotubes of the invention.

These studies, summarized in FIG. 5, clearly show that the labeling of the carbon nanotubes by means of the method of the invention is amply sufficient for studying what becomes of them in vivo. The level of carbon 14-radiolabeling of the carbon nanotubes, as carried out by means of the method of example 2, makes it possible to obtain detection thresholds that are entirely noteworthy, since, with the imagers used, it is possible to detect as little as 100 pg of nanotubes/$mm^2$.

Supplementary optical microscopy studies carried out on the target organs and on the excreta confirm that the radioactivity observed is indeed associated with the presence of carbon nanotubes.

The invention claimed is:

1. A method of radiolabeling carbon nanotubes comprising one or more surface carboxyl groups, characterized in that it comprises at least the following steps:
   a) a step of substituting the surface carboxyl groups with radiolabeled nitrile groups, consisting in reacting, in an organic solvent, said carbon nanotubes with a carbon 13 radiolabeled or carbon 14-radiolabeled cyanide, in the presence of a palladium catalyst, so as to result in radiolabeled carbon nanotubes comprising, at the surface, one or more carbon 13 labeled or carbon 14-labeled nitrile groups; and
   b) a step of hydrolyzing the nitrile group(s), consisting in reacting, in an organic solvent or an aqueous organic mixture, the carbon nanotubes obtained above in step a) with an acid or a base so as to result in radiolabeled carbon nanotubes comprising, at the surface, one or more carboxyl groups in which the carbon atom bearing the acid function is a carbon 13 or carbon 14 atom.

2. The method as claimed in claim 1, characterized in that substitution step a) is carried out in a single step, by cyanating decarboxylation of the surface carboxyl groups in the presence of a palladium catalyst.

3. The method as claimed in claim 2, characterized in that the palladium catalyst is chosen from palladium (II) salts.

4. The method as claimed in claim 3, characterized in that the palladium (II) salts are chosen from palladium trifluoroacetate, palladium sulfate and palladium nitrate.

5. The method as claimed in claim 2, characterized in that the solvent of step a) is chosen from dimethylformamide (DMF), dimethyl sulfoxide (DMSO) and water, and mixtures thereof.

6. The method as claimed in claim 5, characterized in that the organic solvent of step a) is DMF alone or as a DMF/DMSO mixture, in a volume ratio ranging from 100/0 to 80/20.

7. The method as claimed in claim 2, characterized in that cyanating decarboxylation step a) is carried out at a temperature of 25 to 150° C.

8. The method as claimed in claim 2, characterized in that cyanating decarboxylation step a) is carried out in the presence of a silver or copper salt.

9. The method as claimed in claim 8, characterized in that the silver or copper salts are chosen from silver carbonates, nitrates and triflates or copper carbonates, nitrates and triflates.

10. The method as claimed in claim 2, characterized in that the duration of cyanating decarboxylation step a) ranges from 1 to 12 hours.

11. The method as claimed in claim 1, characterized in that substitution step a) comprises the following three substeps:
   a1) a substep of substituting the hydroxyl groups of said surface carboxyl groups with halide groups, consisting in reacting said carbon nanotubes with a halogenating agent, optionally in the presence of an organic solvent, so as to result in carbon nanotubes comprising, at the surface, one or more acid halide groups;
   a2) a second substep of substituting the halogen atom of said acid halide groups with a radiolabeled nitrile group, consisting in reacting, in an organic solvent, the carbon nanotubes obtained above in step a1) with a carbon 13-radiolabeled or carbon 14-radiolabeled cyanide, so as to result in radiolabeled carbon nanotubes comprising, at the surface, one or more carbon 13-labeled or carbon 14-labeled ketonitrile groups;
   a3) a third substep of decarbonylating said ketonitrile groups, consisting in reacting, in an organic solvent, the radiolabeled carbon nanotubes obtained above in step a2) in the presence of a catalyst chosen from palladium0 (Pd0) salts and complexes, so as to result in radiolabeled carbon nanotubes comprising, at the surface, one or more carbon 13-labeled or carbon 14-labeled nitrile groups.

12. The method as claimed in claim 11, characterized in that the halogenating agent used in substep a1) is chosen from thionyl dichloride ($SOCl_2$), oxalyl chloride (ClCOCOCl), phosphorus trichloride ($PCl_3$) and phosphorus pentachloride ($PCl_5$).

13. The method as claimed in claim 11, characterized in that the palladium0 salts and complexes used in substep a3) are chosen from tetrakis(triphenylphosphine)palladium (Pd$(PPh_3)_4$), and also from the pairings palladium$^{II}$ acetate/triphenylphosphine (Pd$(OAc)_2$/TPP), palladiumII acetate/tributylphosphine (Pd(OAc)$_2$/TBP) and palladium$^{II}$ acetate/tricyclohexylphosphine (Pd(OAc)$_2$/PCy$_3$).

14. The method as claimed in claim 11, characterized in that the organic solvent(s) that can be used for implementing substeps a1), a2) and a3) is (are) chosen from toluene, acetonitrile, benzene, dimethylformamide and dioxane, and mixtures thereof.

15. The method as claimed in claim 11, characterized in that step a3) is carried out in the presence of a nucleophilic compound.

16. The method as claimed in claim 15, characterized in that the nucleophilic compound is chosen from cesium fluoride (CsF), potassium fluoride (KF) and potassium cyanide (KCN).

17. The method as claimed in claim 11, characterized in that step a1) is carried out at a temperature of 25 to 120° C.; step a2) is carried out at a temperature of 25 to 120° C., and step a3) is carried out at a temperature of 50 to 120° C.

18. The method as claimed in claim 11, characterized in that substep a2) is carried out in the presence of an iodide salt.

19. The method as claimed in claim 18, characterized in that the iodide salt is chosen from sodium iodide, tetrabutylammonium iodide and potassium iodide.

20. The method as claimed in claim 1, characterized in that the radiolabeled cyanide is chosen from cyanide, trimethylsilyl cyanide, metal cyanides, it being understood that, in these cyanides, the carbon atom involved in the triple bond with the nitrogen atom is a carbon 13 or carbon 14 atom, and from the cyanide derivatives of formula (I) below:

in which:

R$_1$ and R$_2$, which may be identical or different, represent a C$_1$-C$_4$ alkyl radical, or else R$_1$ and R$_2$ form, together with the carbon atom to which they are attached, a hexane ring; and

*C represents a carbon 13 or carbon 14 atom.

21. The method as claimed in claim 20, characterized in that the compounds of formula (I) are chosen from carbon 13-labeled or carbon 14-labeled acetone cyanohydrin and carbon 13-labeled or carbon 14-labeled cyclohexanone cyanohydrin.

* * * * *